(12) United States Patent
Freund

(10) Patent No.: US 7,526,875 B2
(45) Date of Patent: May 5, 2009

(54) COLLIMATOR BLADE ALIGNING DEVICE, COLLIMATOR BLADE ALIGNING APPARATUS AND METHOD FOR PRODUCING A RADIATION COLLIMATOR

(75) Inventor: Andreas Freund, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/976,804

(22) Filed: Oct. 29, 2007

(65) Prior Publication Data

US 2008/0098608 A1 May 1, 2008

(30) Foreign Application Priority Data

Oct. 30, 2006 (DE) ........................ 10 2006 051 146

(51) Int. Cl.
*G01B 5/25* (2006.01)
*G01B 5/14* (2006.01)
*G01K 5/02* (2006.01)
(52) U.S. Cl. ........................................ 33/645; 378/147
(58) Field of Classification Search .................. 33/613, 33/645; 378/147
See application file for complete search history.

(56) References Cited

U.S. PATENT DOCUMENTS 4,376,338 A * 3/1983 Wickham ................... 33/645
5,757,881 A 5/1998 Hughes
5,859,893 A * 1/1999 Moorman et al. ........... 378/147
5,933,975 A * 8/1999 Pate ............................ 33/645
6,600,810 B1 7/2003 Hughes
7,127,037 B2 * 10/2006 Bowen et al. ............... 378/147
7,305,774 B1 * 12/2007 Whaley ....................... 33/613
2007/0064866 A1 * 3/2007 Hsieh et al. ................. 378/147
2008/0273663 A1 * 11/2008 Zhang et al. ................ 378/147

FOREIGN PATENT DOCUMENTS

WO    WO 2006092575 A1    9/2006

OTHER PUBLICATIONS

German Office Action Jan. 16, 2008.

\* cited by examiner

*Primary Examiner*—G. Bradley Bennett
(74) *Attorney, Agent, or Firm*—Harness, Dickey & Pierce, P.L.C.

(57) ABSTRACT

A collimator blade aligning device, a collimator blade aligning apparatus and a method for producing a radiation collimator are disclosed. For the purpose of particularly simple and accurate alignment of the collimator blades, at least one embodiment provides that the collimator blade aligning device can be rotated between a positioning position and aligning position, a first thickness assigned to the positioning position being smaller than, and a second thickness assigned to the aligning position being equal to the blade spacing.

21 Claims, 5 Drawing Sheets

COLLIMATOR BLADE ALIGNING DEVICE, COLLIMATOR BLADE ALIGNING APPARATUS AND METHOD FOR PRODUCING A RADIATION COLLIMATOR

PRIORITY STATEMENT

The present application hereby claims priority under 35 U.S.C. §119 on German patent application number DE 10 2006 051 146.8 filed Oct. 30, 2006, the entire contents of which is hereby incorporated herein by reference.

FIELD

Embodiments of the invention generally relate to a collimator blade aligning device, such as one for aligning two neighboring collimator blades of a radiation collimator in accordance with a given blade spacing during the production thereof for example; a collimator blade aligning apparatus comprising a number of collimator blade aligning devices; and/or a method for producing a radiation collimator by using the collimator blade aligning apparatus.

BACKGROUND

During X-ray imaging, an object to be examined by way of X radiation generally causes scattering of an X radiation emanating from a focus in the direction of a radiation detector. The scattered radiation leads to a distortion of the attenuation values, acquired with the detector, of the X radiation and, finally, to artifacts in the X-ray images produced. In order to suppress and/or absorb the scattered radiation, use is made of scattered radiation collimators, also denoted as radiation collimators, placed directly upstream of the detector.

As a rule, the radiation collimators comprise a multiplicity of thin plane parallel collimator blades, absorption surfaces of juxtaposed collimator blades facing one another. In order to absorb the X radiation, the collimator blades are produced from a material that strongly absorbs the X radiation. Collimator blades produced from metal are also termed collimator plates.

For the purpose of acquiring the X radiation, it is known to use a detector with a multiplicity of individual detector elements that are arranged in a linear fashion, for example like a matrix. In order to avoid crosstalk between neighboring detector elements, the latter are separated from one another by septa.

In order to avoid shading of the detector elements by the collimator blades that is deleterious to the image quality, it is necessary for the collimator blades to be aligned exactly in the beam path of the X radiation and to be positioned precisely over the septa.

To this end, during production of the radiation collimator it is known firstly to position and align the collimator blades with accurate spacing by way of a holder. Subsequently, the collimator blades are interconnected and fixed. By way of example, use is made for fixing purposes of fixing elements with comblike serrations that are introduced into spaces formed between the collimator blades, and are bonded to the collimator blades by way of an adhesive.

A disadvantage here is that the thin and mechanically unstable collimator blades can easily be flexed or bent in conjunction with shrinkage of the adhesive normally occurring upon hardening of the latter. Consequently, the previously exact alignment of the collimator blades is changed. Impairment of the alignment can also be caused by the fitting of the fixing element or by other effects during production.

The result of this is that the collimator blades can no longer be positioned exactly over the septa, and so shading of detector elements cannot be reliably avoided despite an exact positioning of the radiation collimator. This detracts from the sensitivity of the detector and leads unavoidably to artifacts in the X-ray images.

SUMMARY

In at least one embodiment of the invention, at least one of the disadvantages of the prior art is reduced or even eliminated. In particular, one aim of at least one embodiment may be to specify a collimator blade aligning device with the aid of which collimator blades of a radiation collimator can be aligned during production of the latter with particular exactitude and in a simple way. A further aim of at least one embodiment of the invention may be to specify a collimator blade aligning apparatus that enables particularly simple production of a radiation collimator in conjunction with accurate alignment of the collimator blades. Furthermore, a simple and cost effective method may be specified with the aid of which a radiation collimator can be produced with exactly aligned collimator blades.

According to at least one embodiment of the invention, there is provided a collimator blade aligning device for aligning mutually facing absorption surfaces of two neighboring collimator blades of a radiation collimator in accordance with a given blade spacing during the production thereof, having an aligning section of rod type design that can be positioned parallel to the longitudinal axis in a positioning position at a given distance along at least one absorption surface and can be rotated into an aligning position in order to align the collimator blade, and which has with reference to a first direction running perpendicular to its longitudinal axis a first thickness which is assigned to the aligning position and is substantially equal to the blade spacing, and which aligning section has a second thickness which is assigned to the positioning position with reference to a second direction running perpendicular to the longitudinal axis and transverse to the first direction and is smaller than the blade spacing.

During production of the radiation collimator, the collimator blades are generally positioned and aligned by way of a holding apparatus. In this preassembled state, it is possible in each case for a collimator blade aligning device, which is denoted below as aligning device for reasons of simplification, to be arranged in the positioning position at a given spacing along mutually averted absorption surfaces of each collimator blade. Here, the term spacing is to be understood in the abovementioned sense in such a way that the aligning section just fails to touch the absorption surface, that is to say is positioned at the absorption surface. In the case of collimator blades lying inside in neighboring pairs, the aligning device can be introduced into interspaces formed between neighboring collimator blades. To this end, the aligning device can be introduced into the interspaces parallel to their longitudinal axis, the aligning device being located in the positioning position that is assigned the second thickness. Aligning sections are positioned in a corresponding way at the absorption surfaces lying on the outside. Given that the second thickness is smaller than the blade spacing, the aligning device can be introduced and positioned with particular ease. Damage to or deformation of the collimator blades when being introduced and/or positioned can be avoided. In the case of introduction between neighboring collimator blades, the second direction is preferably perpendicular to a middle plane of mutually facing absorption surfaces.

After positioning of the aligning device, the aligning section is located along the absorption surfaces. The collimator blades can be aligned by rotating the aligning position. In this case, the aligning device can be rotated in such a way that the first direction now lies perpendicular to the middle plane. Given that the first thickness assigned to the aligning position is substantially equal to the blade spacing, the collimator blades can be aligned precisely and reliably in a simple way. After fixing of the collimator blades, the aligning device can be rotated back into the positioning position and removed again.

According to one refinement of at least one embodiment of the aligning device, a cross section, running perpendicular to the longitudinal axis, of at least the aligning section is circular, triangular, rectangular or flattened at two opposite sides, in particular is oval. Such aligning device can be produced in a particularly simple and cost effective way with especially small thickness tolerances. The first thickness can in this case be constant along the longitudinal axis. In this case, the longitudinal axis can run in the aligning position parallel to at least one or two mutually facing absorption surfaces. The latter is possible both for collimator blades arranged in parallel, and for ones arranged in fan shaped fashion. It is also possible for the first thickness to increase or decrease along the longitudinal axis in accordance with a fan shaped alignment of the collimator blades. In this case, the longitudinal axis can run in the aligning position in the direction of the fan of collimator blades.

According to a further refinement of at least one embodiment of the aligning device, at least one bearing section is provided for rotatably bearing the aligning device about its longitudinal axis in at least one corresponding cutout of a collimator blade aligning apparatus. In order to be able to ensure introduction into the interspace in a fashion free from damage, the bearing section provided at the end of the aligning device that is to be guided through the interspace preferably has a diameter that is smaller than the blade spacing along the guide path through the interspace. An exact rotation of the aligning device without bearing play can be ensured by suitably adapting the bearing section(s) to the corresponding cutouts, thereby enabling a particularly accurate alignment of the collimator blades.

It is particularly advantageous when there is provided with reference to the longitudinal axis outside the aligning section a drive section for engaging a drive device to rotate the collimator blade aligning device at least between the positioning position and the aligning position. The drive section is preferably provided at the end that is not to be guided through the interspace. With reference to the longitudinal axis, the drive section can be designed in the circumferential direction in the form of a gearwheel, slot or keyway. A drive device designed as a gearwheel, gear rack, spiral spring, strip, V-belt, V-ribbed belt or toothed belt can engage in the drive section so designed. The absorption surfaces can be aligned particularly accurately and in an automated fashion by way of the drive section and drive device, which can comprise, in particular, a motor and the like.

At least one embodiment of the invention further provides a collimator blade aligning apparatus for producing a radiation collimator having a multiplicity of collimator blades, in the case of which absorption surfaces of neighboring collimator blades arranged with a given blade spacing face one another, comprising a number of inventively designed aligning device and a holding apparatus with at least one holding device for holding the collimator blades in accordance with the blade spacing.

The collimator blade aligning apparatus, which is denoted below as aligning apparatus for the sake of simplicity, enables a particularly exact and simple alignment of the collimator blades because of the aligning device provided.

In one refinement of at least one embodiment of the aligning apparatus, it is provided that the holding apparatus comprises two opposite holding plates in congruent arrangement on which the holding device(s) are provided, cutouts in pairwise alignment that are assigned to the collimator blade aligning device and run perpendicular to the holding plate being provided in the holding plates in such a way that each collimator blade aligning device can be guided parallel to the longitudinal axis thereof through at least one of these cutouts in the positioning position, and in that the aligning section can be positioned between the holding plates on a blade plane corresponding to an absorption surface of a collimator blade that can be held in the holding apparatus.

Neighboring cutouts are preferably arranged mutually offset in a plane parallel to the holding plates. It can thereby be ensured that webs or walls formed in the holding plate between neighboring cutouts have sufficient mechanical stability.

According to one refinement of at least one embodiment of the aligning apparatus, the holding device(s) comprise slots for plugging in the collimator blades and/or clamping elements for clamping in the collimator blades between the holding plates. The collimator blades can be held particularly reliably by way of the slots and, in particular the clamping elements.

It is particularly advantageous when the aligning apparatus comprises a drive unit comprising at least the drive device. The drive unit can comprise a motor. The aligning device can thereby be rotated at least between positioning position and aligning position in a simple way. In order to achieve a particularly compact design of the aligning apparatus, the drive unit, that is to say the drive device and, if appropriate, the motor, can be designed in a fashion integrated in one of the holding plates.

Reference may be made to the designs for the aligning device for further advantageous effects of the aligning apparatus and refinements thereof.

At least one embodiment of the invention further provides a method for producing a radiation collimator having a multiplicity of collimator blades, in the case of which absorption surfaces of neighboring collimator blades arranged at a given blade spacing face one another. The production may be performed by using at least one embodiment of the aligning apparatus. At least one embodiment of the method includes:
 a) equipping the holding device with collimator blades,
 b) positioning the aligning device located in the positioning position on the absorption surfaces,
 c) aligning the collimator blades in accordance with a given blade spacing by rotating the aligning device into the aligning position,
 d) connecting and fixing the collimator blades,
 e) rotating the collimator blade aligning device from the aligning position into the positioning position, and removing the collimator blade aligning device, and
 f) detaching the interconnected collimator blades from the holding device, and removing the holding apparatus.

At least one embodiment of the proposed method is particularly easy to carry out and enables an exact and reliable alignment of the collimator blades even when, for fixing, use is made of an adhesive that exhibits shrinkage effects upon hardening.

If the aligning apparatus exhibits the cutouts for plugging in the aligning device, it is possible that in step b) the collimator blade aligning device are introduced into the cutouts in a fashion parallel to their longitudinal axis in such a way that an aligning section lies in each case at mutually averted absorption surfaces on each collimator blade. To this end, precisely one aligning section can respectively be positioned in each interspace formed between neighboring collimator blades and, correspondingly, on the absorption surfaces lying on the outside. The aligning sections can be positioned in the middle between the absorption surfaces of neighboring collimator blades and, correspondingly, on the absorption surfaces lying on the outside.

The collimator blade aligning device can be rotated automatically, preferably synchronously, by way of a drive unit in steps c) and e). This simplifies the production and enables an exact alignment of the collimator blades.

For the purposes of connecting and fixing in step d), a fixing element having comb-like serrations can be fitted on the collimator blades in such a way that the serrations project in the direction of the aligning device, and each collimator blade is held between two serrations, and in which at least the serrations are bonded to the collimator blades by way of an adhesive. The collimator blades can thereby be interconnected in a particularly firm and reliable fashion.

BRIEF DESCRIPTION OF THE DRAWINGS

Example embodiments are explained below in more detail with the aid of the drawings, in which.

Identical or functionally identical elements are denoted in each case by identical reference symbols in the figures. The figures are not necessarily true to scale, and scales can vary between the figures.

DETAILED DESCRIPTION OF THE EXAMPLE EMBODIMENTS

Figure 1:
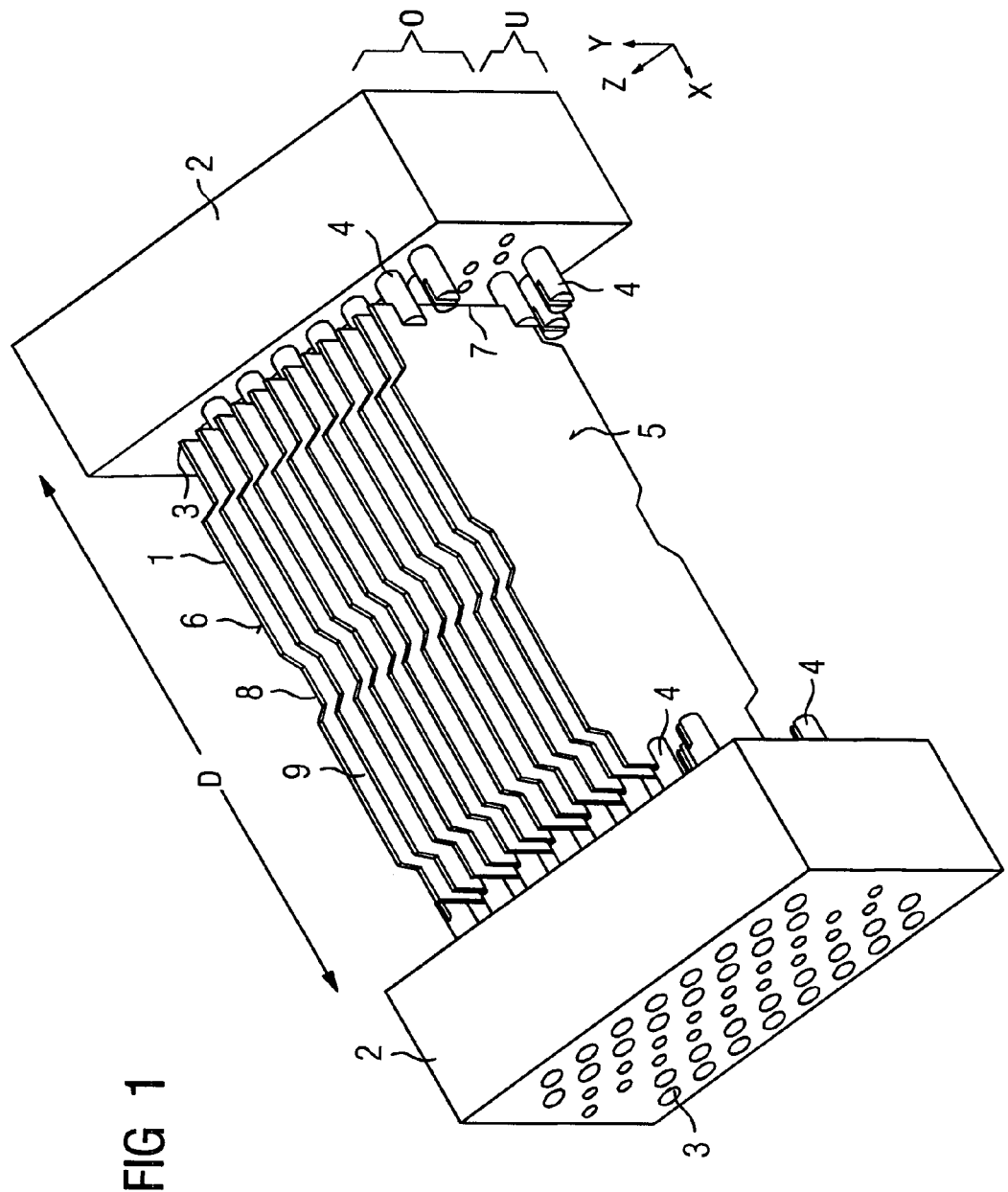
FIG. 1 shows a perspective view of a holding apparatus, equipped with collimator blades, of an aligning apparatus.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows a perspective view of a holding apparatus, only partially equipped with collimator blades 1, of an aligning apparatus.

The holding apparatus comprises two holding plates 2 congruently opposed with reference to an X-direction X. The holding plates 2 are fastened on a baseplate (not shown). With reference to a Y-direction Y, each holding plate 2 has in an upper region O and a lower region U a multiplicity of clamping elements 4, held in corresponding bores 3, for clamping the collimator blades 1 between the holding plates 2. Two clamping elements 4 lie opposite one another in pairs in the X-direction X, in each case.

Clamping elements in opposing pairs are also referred to below as a clamping element pair. Both in the upper region O and in the lower region U, neighboring clamping element pairs for neighboring collimator blades 1 in a Y-direction Y and a Z-direction Z are arranged offset from one another, the clamping elements 4 forming parallel rows in the Z-direction Z. The clamping element pairs are arranged in such a way that, after being clamped in, the collimator blades 1 are aligned in the shape of a fan with a fictitious focus, the focus being able, of course, to lie at infinity, which device that the clamping element pairs for holding the same collimator blade 1 lie one above another, and the collimator blades are parallel.

The collimator blades 1 are of rectangular design and are arranged such that absorption surfaces 5 of two neighboring collimator blades 1 face one another. The collimator blades 1 are held in their longitudinal direction between the holding plates 2, their long sides 6 running in the X-direction X, and their transverse sides 7 in the Y-direction Y. The collimator blades are held at the edges of the transverse sides 6 in the upper region O and lower region U, in each case by way of a clamping element pair. On the long sides 6, the collimator blades have incisions 8 for positioning a fixing element (not shown in FIG. 1) described further below.

Equipping the holding apparatus with collimator blades 1 in accordance with FIG. 1 constitutes a first step in the production of a radiation collimator. In the state illustrated in FIG. 1, the collimator blades 1 are held by way of the clamping elements 4. However, because the clamping elements 4 are not of a particularly stable design in mechanical terms, they are virtually unable to produce an aligning effect for uneven and/or bent collimator blades in the middle region between the holding plates. For example, given a collimator blade thickness of 0.1 mm in the region of the clamping elements 4 it is possible to achieve a positioning accuracy of less than 0.005 mm, while a positional deviation of the collimator blades 1 of up to 0.06 mm can come about in the middle region.

Figure 2:
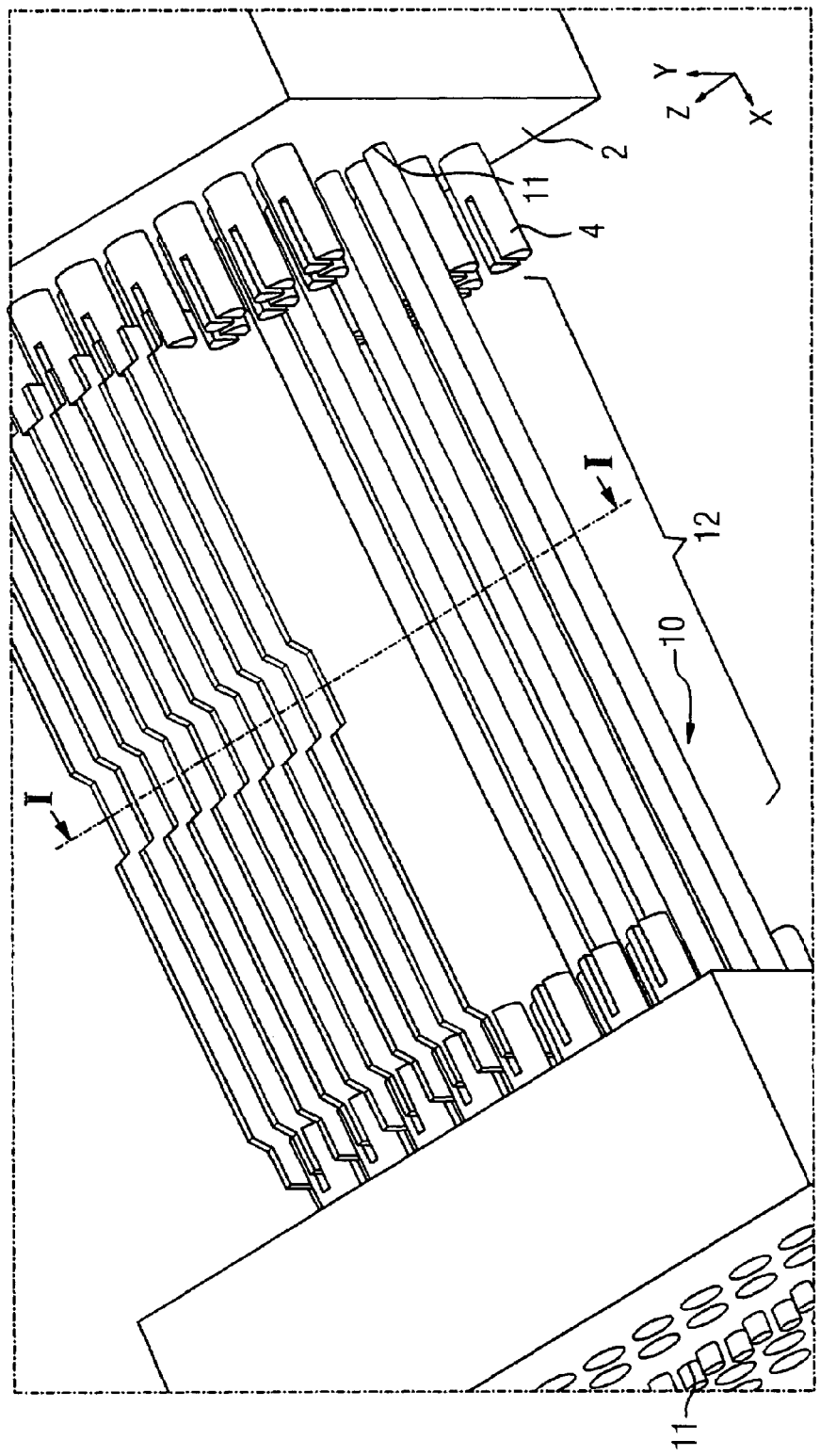
FIG. 2 shows the aligning apparatus of FIG. 1 with aligning device that are positioned on the collimator blades.

In order to reduce the positional deviation and to prevent the latter from being enlarged further during the production process, an aligning device 10 aligned in accordance with a positioning position is positioned in each interspace 9 formed between opposite absorption surfaces 5 of the collimator blades 1. To this end, cutouts 11 or cutout pairs aligned in pairs in the X-direction X are provided in the holding plates 2. An aligning device 10 is plugged into each cutout pair such that an aligning section 12 is present at each absorption surface in the X-direction X. In this case, bearing sections (not shown) lying on both sides of the aligning section 12 are held rotatably in the cutouts 11. The cutouts 11 thus serve, in particular, as abutment for the bearing sections and, in addition to a simple introduction, enable a simple and particularly accurate rotation of the aligning device 10 about the longitudinal axis 13 thereof. The cutout 11 of the left-hand holding plate 2 of FIG. 2 is provided as through hole for plugging the aligning device 10 through, while the cutout 11 on the right-hand holding plate 2 of FIG. 2 is designed as a blind hole. In order to align the collimator blades, the aligning device 10 positioned in such a way is rotated from the positioning position into the aligning position. The final state after the collimator blades 1 have been introduced and aligned is illustrated in FIG. 2.

Figure 3:
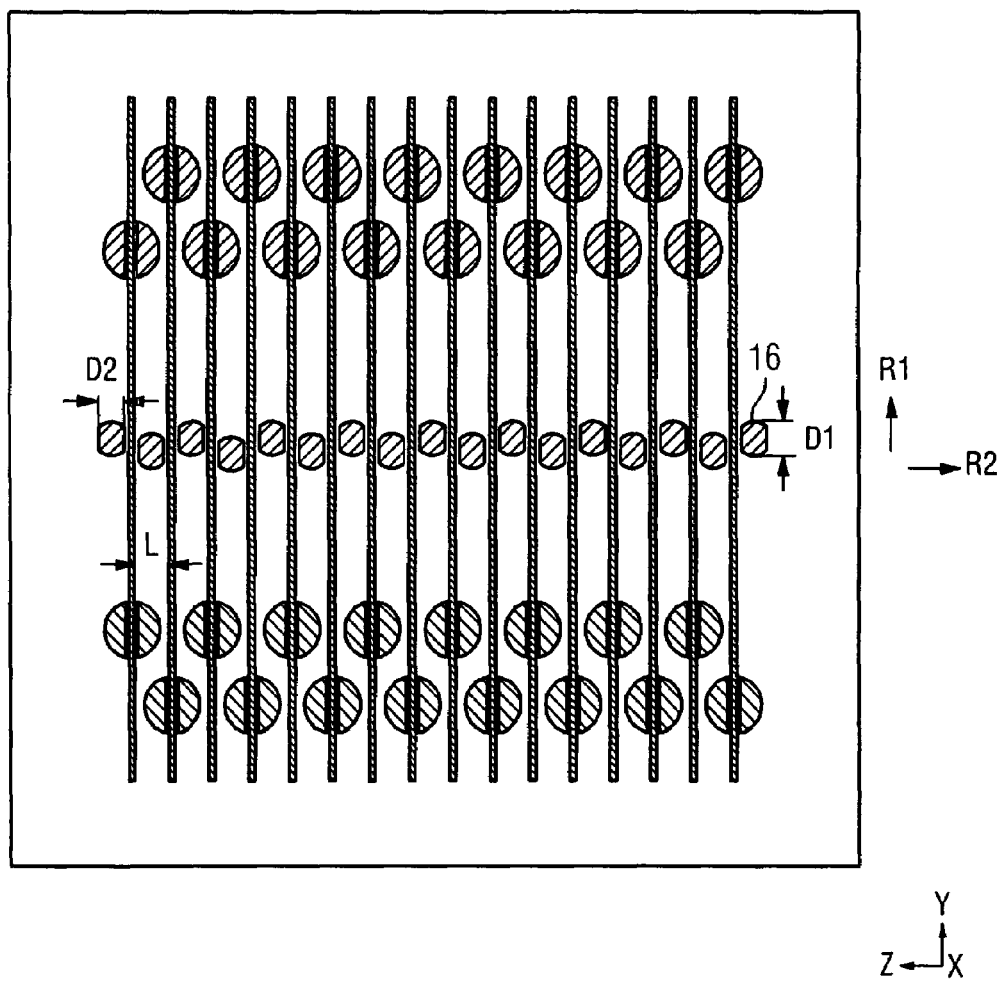
FIG. 3 shows a first cross section along the line I-I of FIG. 2.
Figure 4:
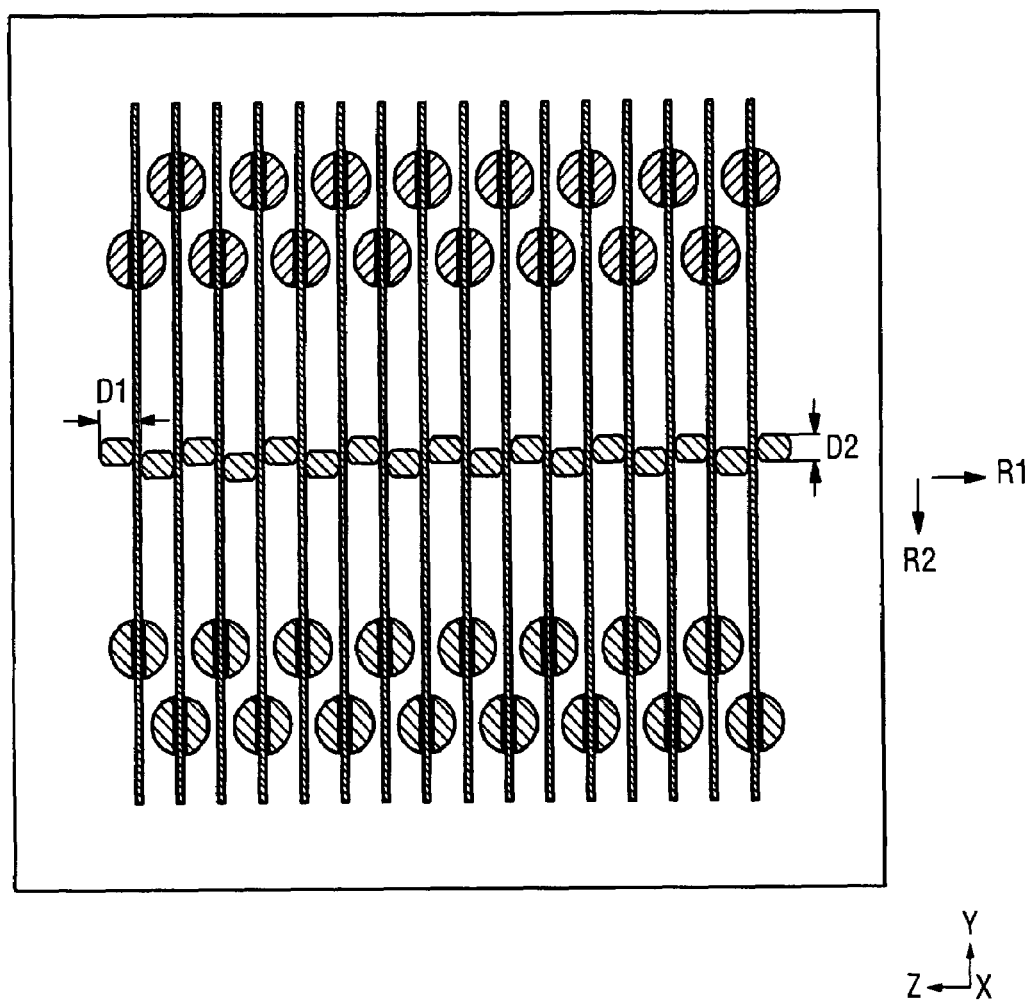
FIG. 4 shows a second cross section along the line I-I of FIG. 2.

In order to explain the positioning of the aligning device 10 and the alignment of the collimator blades 1, FIGS. 3 and 4 show two different cross sections along a line I-I of FIG. 2 before and after the alignment.

The aligning device 10 are illustrated in FIG. 3 in the positioning position and, by contrast, in FIG. 4 in a fashion rotated at an angle of 90 degrees in the aligning position. As is to be gathered from FIGS. 3 and 4, the aligning section 12 has a first thickness D1, assigned to the aligning position, with reference to a first direction R1 running perpendicular to the longitudinal axis 13, and a second thickness D2, assigned to the positioning position, with reference to a second direction R2 running perpendicular to the longitudinal axis 13 and perpendicular to the first direction R1. The second thickness D2 is smaller than a blade spacing L between mutually facing absorption surfaces 5 at the level of the course of the longitudinal axes 13 of the aligning device 10. By contrast, the first thickness D1 is substantially equal to the blade spacing L.

It is possible to achieve with this advantageous refinement of the alignment section 12 with different thicknesses that the aligning device 10 can, without touching the collimator blades 1 or sliding along them, be positioned in the positioning position at the absorption surfaces 5 and be removed therefrom in a simple way. Given that the aligning device 10 are rotatably supported, the latter can be rotated from the positioning position into the aligning position with particular ease and reliability after being introduced, it thereby being possible to achieve a particularly accurate and reliable alignment of the collimator blades 1 in accordance with the first thickness D1 and the blade spacing.

Figure 5:
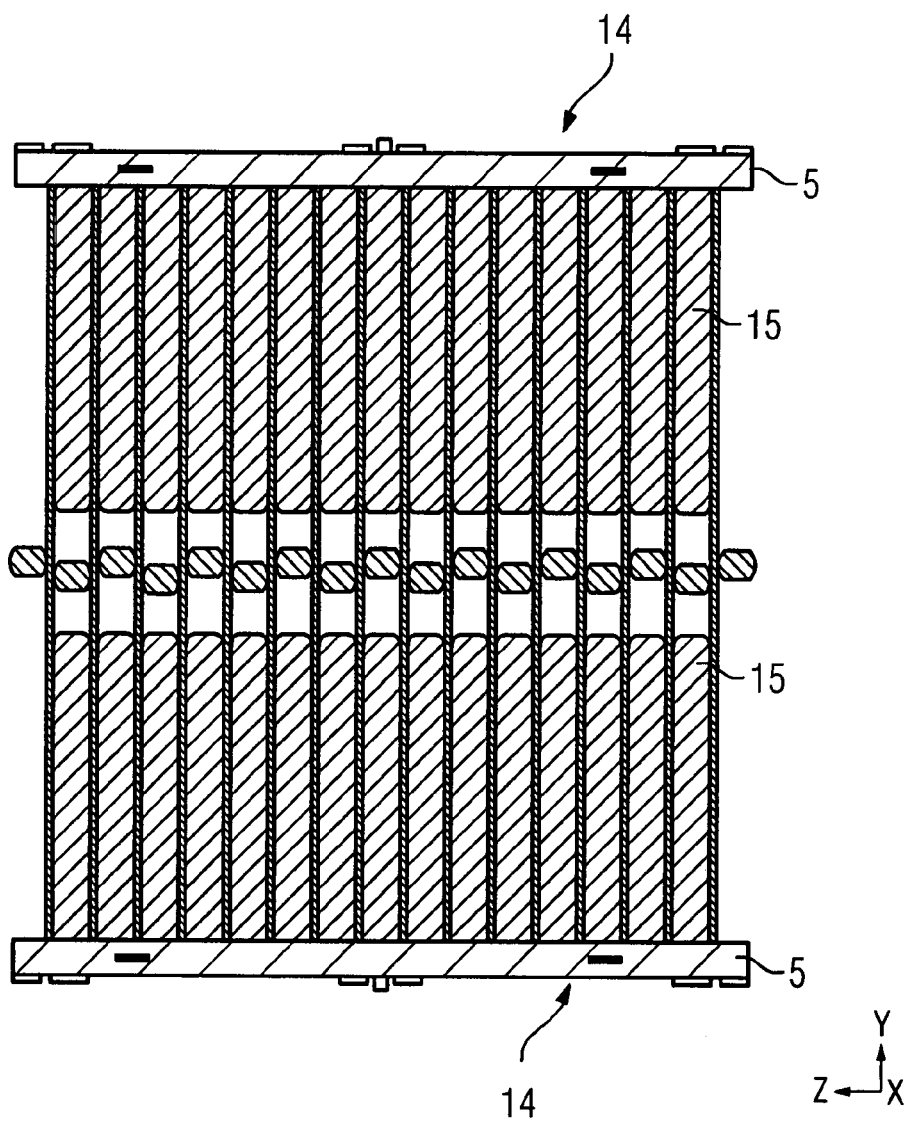
FIG. 5 shows a third cross section corresponding to FIG. 4, fixing elements being fitted on the collimator blades.

The exactly aligned collimator blades 1 can now be connected to form a radiation collimator. In this case, the collimator blades 1 are respectively interconnected at the upper and lower longitudinal sides 5 by way of a fixing element 14, as is shown in a third cross section in FIG. 5. The fixing element 14 has serrations 15 whose thickness corresponds to the desired blade spacing L. The fixing element 14 is fitted in such a way that each collimator blade 1 is held between two serrations 15, and the serrations 15 project in the direction of the aligning device 10. An adhesive is used to fix and fasten the fixing element 14 and the serrations 14 on the collimator blades 1. The serrations 15 do not extend entirely as far as the aligning elements 10, and so it is possible to avoid being stuck to the serrations 15 or collimator blades 1. The aligning device 10 can be removed when the adhesive has hardened. This can be performed in the reverse sequence to the positioning and alignment, and is not explained further.

Because of the advantageously designed aligning section 12, there is no problem in positioning the aligning device 10 in the positioning position, nor are the collimator blades 1 damaged or bent. Rotation into the aligning position renders it possible to ensure that the collimator blades 1 are exactly aligned, and that the alignment is not impaired in the course of the production process. The aligning device 10 can be used to align slightly flexed collimator blades 1 rectilinearly. It is possible to prevent the collimator blades 1 from being additionally flexed as a consequence of adhesive shrinkage. It is thereby possible to extend the permitted shape tolerance of the collimator blades 1 in the case of a collimator blade thickness of 0.1 mm to 0.120 mm by comparison with the 0.07 mm currently allowed, and this is attended by substantial minimization of costs.

Furthermore, it is possible to reduce the position tolerance from currently 0.06 mm to 0.03 mm. It is possible with the aid of a higher positioning accuracy of the collimator blades 1 of the radiation collimator to prevent collimator blades 1 from shading detector elements of a detector comprising the radiation collimator. As a consequence of the more accurate overall alignment of the collimator blades 1 that can be achieved with the aid of aligning device 10, it is, in particular also possible to reduce a width of the septa provided between the detector element from currently 0.29 mm to 0.23 mm. As a result of this, a detection surface of the detector elements can be enlarged, and the efficiency and the sensitivity of the detector can be raised.

The exact and reliable alignment of the collimator blades 1 gives rise to preconditions that are required to automate the production of the radiation collimator, in particular the fixing of the fixing elements 14 on the collimator blades 1.

Finally, it is also advantageous for automating the production that the aligning device 10 can be rotated by way of a drive unit that is, for example, integrated in one of the holding plates 2. The drive unit enables uniform and precise rotation such that a constant quality of the radiation collimators can be ensured.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A collimator blade aligning device for aligning mutually facing absorption surfaces of two neighboring collimator blades of a radiation collimator in accordance with a given blade spacing during the production thereof, comprising:
   an aligning section, of rod type design, positionable parallel to a longitudinal axis in a positioning position at a given distance along at least one absorption surface and rotatable into an aligning position to align the collimator blade and which has, with reference to a first direction running perpendicular to its longitudinal axis, a first thickness assigned to the aligning position and substantially equal to the given blade spacing, wherein the aligning section includes a second thickness assigned to the positioning position with reference to a second direction running perpendicular to the longitudinal axis and transverse to the first direction and smaller than the blade spacing.

2. The collimator blade aligning device as claimed in claim 1, wherein a cross section, running perpendicular to the longitudinal axis, of at least the aligning section is at least one of circular, triangular, rectangular, flattened, and oval.

3. The collimator blade aligning device as claimed in claim 1, wherein, with reference to the longitudinal axis, the collimator blade aligning device includes, at least in an end region, a bearing section for rotatably bearing the collimator blade aligning device about its longitudinal axis in at least one corresponding cutout of a collimator blade aligning apparatus.

4. The collimator blade aligning device as claimed in claim 1, comprising, with reference to the longitudinal axis outside the aligning section, a drive section to engage a drive device to rotate the collimator blade aligning device at least between the positioning position and the aligning position.

5. The collimator blade aligning device as claimed in claim 4, wherein, with reference to the longitudinal axis, the drive section is designed in the circumferential direction in the form of at least one of a gearwheel, slot and keyway.

6. The collimator blade aligning device as claimed in claim 4, wherein the drive device comprises at least one of a gearwheel, a gear rack, a spiral spring, a strip, a V-belt, V-ribbed belt and a toothed belt.

7. A collimator blade aligning apparatus for producing a radiation collimator having a multiplicity of collimator blades, wherein absorption surfaces of neighboring collimator blades arranged with a given blade spacing facing one another, the collimator blade aligning apparatus comprising:
   a number of collimator blade aligning devices as claimed in claim 1; and
   a holding apparatus with at least one holding device to hold the collimator blades in accordance with the given blade spacing.

8. The collimator blade aligning apparatus as claimed in claim 7, wherein the holding apparatus comprises two opposite holding plates in congruent arrangement, on each of which at least one holding device is provided, cutouts in pairwise alignment that are assigned to the collimator blade aligning device and run perpendicular to the holding plate being provided in the holding plates such that each collimator blade aligning device is guideable parallel to the longitudinal axis thereof through at least one of the cutouts in the positioning position, and wherein the aligning section is positionable between the holding plates on a blade plane corresponding to an absorption surface of a collimator blade that is holdable in the holding apparatus.

9. The collimator blade aligning apparatus as claimed in claim 8, wherein neighboring cutouts are arranged mutually offset in a plane parallel to the holding plates.

10. The collimator blade aligning apparatus as claimed in claim 8, wherein the at least one holding device comprises at least one of slots for plugging in the collimator blades and clamping elements for clamping in the collimator blades between the holding plates.

11. The collimator blade aligning apparatus as claimed in claim 8, further comprising:
   with reference to the longitudinal axis outside the aligning section, a drive section to engage a drive device to rotate the collimator blade aligning device at least between the positioning position and the aligning position; and
   a drive unit, comprising at least the drive device, for rotating the collimator blade aligning device at least between the positioning position and aligning position.

12. The collimator blade aligning apparatus according to claim 11, wherein the drive unit comprises a motor.

13. The collimator blade aligning apparatus as claimed in claim 11, wherein the drive unit is designed in a fashion integrated in at least one holding plate.

14. A method for producing a radiation collimator having a multiplicity of collimator blades, at least one collimator blade aligning device and a holding apparatus with at least one holding device to hold the collimator blades in accordance with a given blade spacing, wherein absorption surfaces of neighboring collimator blades arranged at the given blade spacing face one another, by way of a collimator blade aligning apparatus as claimed in claim 8, the method comprising:
   a) equipping the holding device with collimator blades;
   b) positioning the collimator blade aligning device, located in a positioning position, on the absorption surfaces;
   c) aligning the collimator blades in accordance with the given blade spacing by rotating the collimator blade aligning device into the aligning position;
   d) connecting and fixing the collimator blades;
   e) rotating the collimator blade aligning device from the aligning position into the positioning position, and removing the collimator blade aligning device; and f) detaching the interconnected collimator blades from the holding device, and removing the holding apparatus.

15. The method as claimed in claim 14, wherein in step b), the collimator blade aligning device is introduced into the cutouts in a fashion parallel to their longitudinal axes such that at least one aligning section lies in each case at mutually averted absorption surfaces of each collimator blade.

16. The method as claimed in claim 14, wherein the collimator blade aligning device is rotated automatically by way of a drive unit in steps c) and e).

17. The method as claimed in claims 14, wherein in step d), at least one fixing element having comb-like serrations is fitted on the collimator blades such that the serrations project in the direction of the collimator blade aligning device, and each collimator blade is held between two serrations, and wherein at least the serrations are bonded to the collimator blades by way of an adhesive.

18. The collimator blade aligning device as claimed in claim 2, wherein, with reference to the longitudinal axis, the collimator blade aligning device includes, at least in an end region, a bearing section for rotatably bearing the collimator blade aligning device about its longitudinal axis in at least one corresponding cutout of a collimator blade aligning apparatus.

19. The collimator blade aligning device as claimed in claim 5, wherein the drive device comprises at least one of a gearwheel, a gear rack, a spiral spring, a strip, a V-belt, V-ribbed belt and a toothed belt.

20. The collimator blade aligning apparatus as claimed in claim 9, wherein the at least one holding device comprises at least one of slots for plugging in the collimator blades and clamping elements for clamping in the collimator blades between the holding plates.

21. The collimator blade aligning apparatus as claimed in claim 12, wherein the drive unit is designed in a fashion integrated in at least one holding plate.

* * * * *